United States Patent [19]

Auth et al.

[11] Patent Number: 4,532,924
[45] Date of Patent: Aug. 6, 1985

[54] MULTIPOLAR ELECTROSURGICAL DEVICE AND METHOD

[75] Inventors: David C. Auth, Bellevue; Eric A. Opie, Seattle; Dale M. Lawrence, Lynnwood, all of Wash.

[73] Assignee: American Hospital Supply Corporation, Evanston, Ill.

[21] Appl. No.: 373,652

[22] Filed: Apr. 30, 1982

Related U.S. Application Data

[63] Continuation-in-part of Ser. No. 145,576, May 13, 1980, abandoned.

[51] Int. Cl.³ .............................................. A61B 17/39
[52] U.S. Cl. ................................................. 128/303.17
[58] Field of Search ........................ 128/303.13–303.18

[56] References Cited

U.S. PATENT DOCUMENTS

| | | | |
|---|---|---|---|
| 164,184 | 6/1875 | Kidder | 128/303.14 |
| 1,366,756 | 1/1921 | Wappler | 128/303.14 |
| 1,814,791 | 7/1931 | Ende | 128/303.17 |
| 1,983,669 | 12/1934 | Kimble | 128/303.14 |
| 2,275,167 | 3/1942 | Bierman | 128/303.17 |
| 3,460,539 | 8/1969 | Anhalt, Sr. | 128/303.14 |
| 3,901,242 | 8/1975 | Storz | 128/303.15 |
| 3,902,494 | 9/1975 | Haberlen et al. | 128/303.17 X |
| 3,920,021 | 11/1975 | Hiltebrandt | 128/303.17 |
| 3,974,833 | 8/1976 | Durden | 128/303.17 X |
| 3,987,795 | 10/1976 | Morrison | 128/303.14 |
| 4,011,872 | 3/1977 | Komiya | 128/303.14 |
| 4,033,351 | 7/1977 | Hetzel | 128/303.14 |
| 4,202,337 | 5/1980 | Hren et al. | 128/303.14 |
| 4,228,800 | 10/1980 | Segler et al. | 128/303.14 |
| 4,248,231 | 2/1981 | Herczog et al. | 128/303.14 |

FOREIGN PATENT DOCUMENTS

| | | | |
|---|---|---|---|
| 243478 | 1/1947 | Switzerland | 128/303.18 |
| 644491 | 1/1979 | U.S.S.R. | 128/303.17 |

*Primary Examiner*—Lee S. Cohen
*Attorney, Agent, or Firm*—Perman & Green

[57] ABSTRACT

A multipolar electrosurgical device is described for use in neurosurgery or through the channel of an endoscope or other precision surgery procedures. The device is formed with an insulative probe body, which, in the described embodiment, is sized to pass through a channel of an endoscope to enable the electrocoagulation of blood vessels such as may be needed in the treatment of a gastrointestinal ulcer. The probe body is provided with electrically separate conductors which are formed of a plurality of electrodes distributed over the peripheral surface of the probe body. The electrically separate conductors are so sized in width W and spaced from each other by a distance S as to establish a ratio of W:S which enables effective bipolar treatment of tissue independent of probe body orientation relative to the tissue and without sticking of the probe body to coagulated material. A plurality of at least six electrodes which can form six bipolar electric fields are formed which in one embodiment are aligned longitudinally on the probe body. The electrodes extend onto the probe body's distal end to provide an omnidirectionally effective electrosurgical device. A central conductive wash channel is provided for electrical connection to a set of electrodes at the distal end of the probe body while also providing a passage for fluid to enhance the visibility of the target area for subsequent precise electrocoagulation of the bleeding site. Several embodiments are shown and described.

25 Claims, 7 Drawing Figures

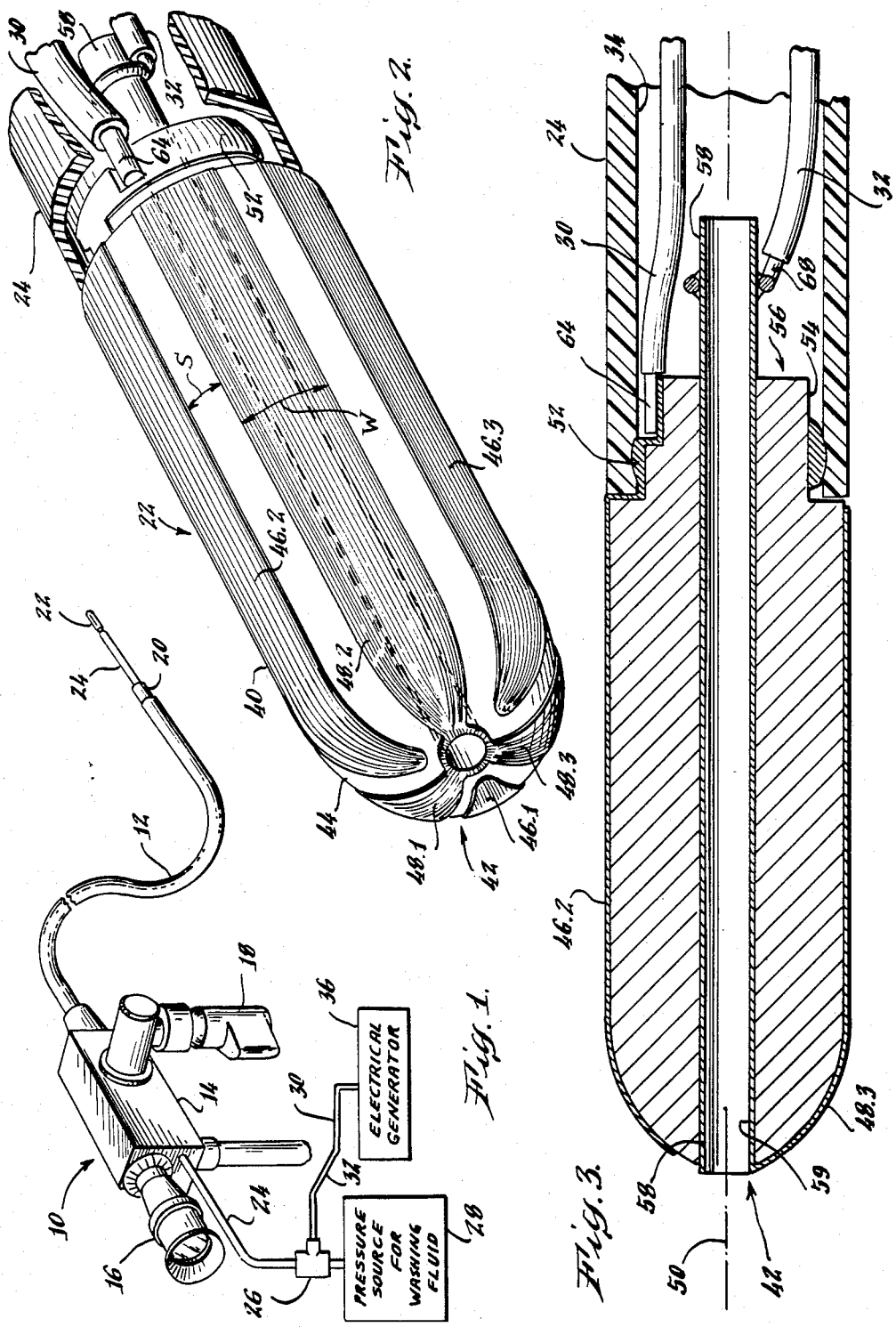

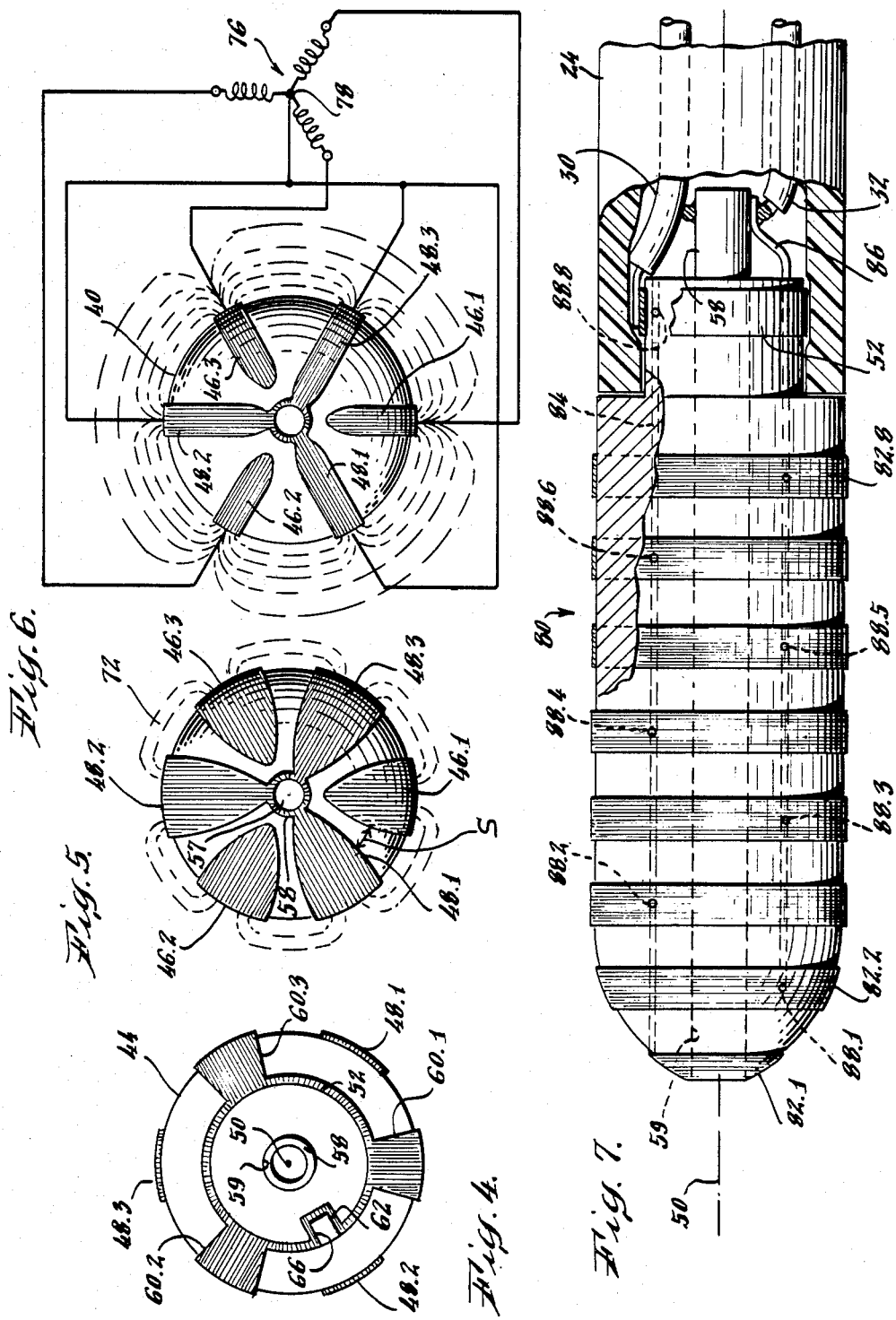

MULTIPOLAR ELECTROSURGICAL DEVICE AND METHOD

PRIOR APPLICATIONS

This application is a continuation-in-part of U.S. patent application Ser. No. 145,576 filed on May 13, 1980, now abandoned.

FIELD OF THE INVENTION

This invention relates to electrosurgery generally, and more specifically to a multipolar electrosurgical device for use in precision surgery such as through an endoscope for the coagulation of tissue or in neurosurgery or eye surgery.

BACKGROUND OF THE INVENTION

The use of heat for the cauterization of bleeding wounds dates to ancient times. In the present century the use of radio frequency (RF) electrical current traveling through a portion of the body has been widely used to stop bleeding. Cauterization of tissue arises by virtue of its resistivity to RF energy. In the cauterization of blood, the proteins in it are heated to a temperature where the proteins congeal similar to the process involving the cooking of egg white. RF energy is preferred because its frequency is above that which could otherwise cause neuro-muscular stimulation. Several modes of RF cauterization of tissue are employed, such as monopolar or bipolar coagulation.

In monopolar coagulation, an active electrode of small dimensions such as of the order of one to two mm is applied to the bleeding site and the current path is completed through the body to a distal plate electrically in contact with a large surface area of the body such as the buttocks. One technique in which the monopolar mode may be employed involves fulguration which is the use of a spark or arc from the active electrode to the tissue. In bipolar coagulation, the two active electrodes are closely spaced, of the order of millimeters so that the current path is confined to a local region of the tissue.

Another technique for stopping bleeding involves the delivery of thermal energy, such as from a resistively heated probe as described in an article entitled "The Heater Probe: A New Endoscopic Method For Stopping Massive Gastrointestinal Bleeding" by David C. Auth et al and appearing in Vol. 74, No. 2, Part 1, pages 257-262 of Gastroentology, 1978. Laser energy has been suggested as described in an article entitled Endoscopic Laser Treatment by David C. Auth et al and appearing at pages 232-239 of the above Gastroentology publication.

A comparison of these various coagulating techniques appears at pages 362-366 of an article entitled "Nonsurgical Management Of Acute Nonvariceal Upper Gastrointestinal Bleeding" by David C. Auth et al and published at page 349 of Hemostasis and Thrombosis, Vol. 4, 1979, Edited by T. H. Spaet, published by Grune & Stratton, Inc. Thus, it is well known that tissue proteins coagulate at temperatures of 50°-100° C.

The coagulation of bleeding vessels such as in the case of bleeding ulcers in gastrointestinal parts of the body requires use of a long endoscope from the distal end of which the bleeding area first must be identified and subsequently treated with an instrument passed through a channel provided in the endoscope. The locating of the bleeding site is not easy since often the tissue wall being investigated may be moving, debris in the form of particles is likely to be present and interfere with vision and the blood flow itself tends to obscure the bleeding sources. These can be very small, of the order of less than a mm with many present in a particular area and each to be coagulated.

The endoscope, or the device put through it, therefore, is also provided with a wash channel through which a fluid such as a liquid or gas can be supplied to flush away the debris and permit visual scrutiny of the tissue area to be treated. In the above identified Endoscope Laser Treatment article, a flow of gas which is coaxial with the laser fiber is used to clear tissue. In a known electrosurgical device of the bipolar type, a pair of conductors are embedded in the wall of a catheter whose central bore is used to supply gas or liquid to the tissue area to be treated. The conductors project in the form of spaced-apart loops from a distal end of the catheter.

When a tissue area is to be treated, each tiny source of blood is subjected to heat treatment. This means the clearing of tissue with a wash of fluid, followed by the application of heat, again clearing the area and applying heat and so on until all of the bleeding areas have been coagulated. In such treatment, the repeated applications should be made with facility in an accurate manner with a minimum of undesirable side effects such as the sticking of the coagulating device to tissue areas. The laser technique has the advantage of not requiring physical contact, and thus avoiding such sticking problems, but because of the variable way in which different tissue conditions permit absorption of the laser energy, precise control during tissue treatment is difficult. The monopolar electrosurgical device tends to injure tissue not intended to be treated and even cause damage in the target area itself such as by excessively deep effects in the target area. Hence, bipolar electrosurgical treatment of tissue has been used and proposed as improving safety because the electric current is confined to the small area between electrodes. Several bipolar devices have been proposed.

For example, starting with an early 1875 U.S. Pat. No. 164,184 to Kidder, a bipolar electrosurgical device is proposed wherein a pair of conductors are spirally wound onto a rubber probe body in which the conductors are embedded. The conductors are shown terminated at a distal hemispherically shaped end of the probe body. A thermally heated knife is described and shown in the U.S. Pat. No. 1,366,756 to R. H. Wappler who employed a pair of half-round cross-sectionally shaped conductor rods twisted about an insulator to connect to a heater-knife. In 1934 Kimble proposed a bipolar electrosurgical device in U.S. Pat. No. 1,983,669 wherein a pair of conductors are shown twisted around a common insulator and project from a retainer body in a manner useful for side-wise or head-on application to a tissue area.

The U.S. Pat. No. 4,011,872 to Komiya proposes an electrosurgical device wherein, for example, as shown in FIGS. 5, 9 and 11, one conductor is connected to a high frequency energy source and is formed of three or four electrodes. The electrodes individually extend from a distal end with spacings between electrodes being variable to accommodate or grasp differently sized tissue areas. In the U.S. Pat. No. 3,987,795 to Morrison, an electrosurgical device is described to operate in a mode which is intermediate between the mono and bipolar modes of electrosurgery. This is achieved by mounting on one body, made of ceramic or glass, an active electrode and a return electrode whose surface area is made significantly larger than that of the active electrode. Various probe configurations are illustrated in the drawings.

Although these prior art electrosurgical devices are useful, they often do not provide satisfactory operation for a number of reasons. For instance, as previously noted, it is important that the probe body with which a cauterizing high frequency current is supplied can be repeatedly and precisely made to impinge upon the tiny blood vessel openings in the tissue area being treated independent of the orientation of the probe. This requires that as the probe is manually controlled at the proximal end of an endoscope, proper electrical contact is achieved to coagulate a blood vessel or other tissue target area whether the probe body is applied head-on, obliquely or side-wise to the tissue area.

Prior art devices such as taught by Kidder, Kimble and Komiya tend to cause hot points at the site being treated, thereby increasing a likelihood of a sticking of the probe body to the coagulated site. As the probe body is withdrawn from the coagulated site to which the probe is sticking bleeding may be restarted and the probe body requires recleaning so that the effectiveness of the entire procedure suffers.

Use of electrode configurations as shown or described in the above prior art, thus frequently is unsatisfactory because of the larger number of probe applications needed to treat a tissue target or achieve coagulation of a bleeding tissue area.

SUMMARY OF THE INVENTION

With an electrosurgical device in accordance with the invention, a more consistent and accurate tissue treatment is obtained with a multipolar probe body on which at least one pair of conductors is distributed in a predetermined manner. As described with respect to one embodiment, the probe body is sized so that it can be passed through a channel of an endoscope from its proximal end. The probe body is provided with conductors which are branched to form a plurality of electrodes. The electrodes of different conductors are selectively sized and generally uniformly distributed in spaced apart pairs, over the distal end and side of the peripheral surface of the probe body. The ratio of the width of the electrodes to the spacing between them is so selected as to provide, with a predetermined minimum number of spaced apart pairs of electrodes, omnidirectional multipolar treatment of tissue when the probe body is operatively projected from the distal end of the endoscope.

The term multipolar, as used herein, means the electrosurgical use of a plurality of conductors which are arranged in fixed relationship with each other on a probe body for at least a bipolar contact with a precise treatment of small tissue targets over a wide range of orientations of the electrosurgical device relative to the tissue target.

As described with reference to one form for an electrosurgical device in accordance with the invention, the probe body is provided with a central bore which extends from the proximal to the distal end of the probe body and is sized to pass a fluid sufficient to clear the tissue area to be treated. The probe body bore may be provided with a conductive lining as part of a conductor along which RF current is supplied to electrodes converging at and connected to the conductive lining at the distal probe body end.

With an electrosurgical device in accordance with the invention, a bleeding tissue area can be approached over a broad range of orientations, yet treated with greater effectiveness and fewer probe applications. A more uniform coagulation is achieved with limited depth of damage and a more predictable zone of coagulation. A mechanically gentle contact with the tissue to be treated can be used.

The use of a multiple number of pairs of electrodes of different conductors assures at least bipolar or multiple bipolar tissue contact when the probe body is applied while the probe body is small enough to electrically coagulate the individual blood vessels from the distal end of an endoscope. A particularly effective probe body in accordance with the invention employs at least six electrodes, constituting the equivalent of six bipolar coagulating devices, around the peripheral surface of the endoscopically passable probe body. With such electrosurgical device, bipolar, tripolar or higher polar tissue contact can be made independent of the orientation of the probe body for effective treatment of tissue such as gastric bleeding ulcers.

It is, therefore, an object of the invention to provide an electrosurgical device which can be reliably applied in an accurate manner in the electrosurgical treatment of small tissue targets.

It is a further object of the invention to provide an electrosurgical device which is passable through an endoscope to coagulate bleeding vessels from the distal end of the endoscope in a reliable and consistent manner. It is a further object of the invention to provide an omnidirectionally effective electrosurgical device with which gastrointestinal bleeding ulcers may be treated in an efficient and effective manner through an endoscope.

These and other advantages and objects of the invention can be understood from the following description of several electrosurgical devices in accordance with the invention which is described in conjunction with the drawings.

BRIEF DESCRIPTION OF DRAWINGS

FIG. 1 is a perspective view of an endoscope instrument with an electrosurgical device in accordance with the invention may be used;

FIG. 2 is a greatly enlarged perspective view of an electrosurgical device in accordance with the invention;

FIG. 3 is a central sectional view along a longitudinal axis of the electrosurgical device in accordance with the invention;

FIG. 4 is a rear end view of the electrosurgical device of FIG. 2 without connecting wires and connecting catheter;

FIG. 5 is a front end view of the electrosurgical device of FIG. 2;

FIG. 6 is a front end view of an electrosurgical device and electrical schematic showing an alternate electrical interconnection for the device; and FIG. 7 is a side view in partial section of an alternate electrosurgical device in accordance with the invention.

DETAILED DESCRIPTION OF EMBODIMENTS

With reference to FIGS. 1 through 4, a conventional endoscope 10 is illustrated. The endoscope 10 has a long flexible shaft 12 though the invention may be used with different fixed shaft endoscopes. At its proximal end the endoscope 10 is provided with a control head 14, a viewer 16 and a joy-stick 18 to control the deflection of the flexible distal end 20 of flexible shaft 12. The flexible shaft 12 has a number of channels to enable viewing by way of flexible fiber optics, a channel to carry a supply of cleaning fluid such as gas or water, and a channel through which special devices can be passed such as a forceps, brush, or knife to carry out a surgical procedure.

The endoscope 10 in FIG. 1 is provided with a bullet-shaped electrosurgical device 22 with which tissue can be treated from the distal end 20 of shaft 12. The electrosurgical device 22 is press-fit connected to the distal end of a long catheter 24 passed through an endoscope 10. Insulated electrical wires 30, 32, which are connected to electrosurgical device 22, are passed through the lumen 34 of catheter 24 and coupling 26 to connect to an RF source 36. Existing electrosurgical generators can be used and, if necessary, simple impedance matching networks employed, such as a resistor across conductors 30, 32. In some instances an isolation transformer is interposed for safety.

The electrosurgical device 22 is formed of an electrically insulative probe body 40 sized to pass from the proximal end to the distal end of an endoscope channel. The probe body 40, as illustrated in FIGS. 2, 3 and 4, is greatly enlarged since, for example, in one practical size its maximum cross-sectional dimension is of the order of 2.4 mm (about 0.095"). The probe body 40 has a generally cylindrical shape with its distal end 42 being smoothly bluntly curved into a generally semi-spherical shape.

The probe body 40 has an outer peripheral surface 44 on which a pair of conductors 46, 48 are placed and respectively electrically connected to wires 30, 32. The conductors 46, 48 are branched to each form three fine longitudinal strip electrodes 46.1, 46.2, 46.3 and 48.1, 48.2, 48.3. The electrodes are aligned generally parallel on peripheral surface 44 with the longitudinal axis 50 of the probe body 40 and are angularly uniformly distributed at angular intervals of 60°. The electrodes of different conductors 46, 48 are respectively successively spaced along each other at distances, S. The gaps S are generally about the same as the widths W of the electrodes at the cylindrical portion of the probe body 40 where the electrodes also are generally of equal size. For a probe body 40 of a 2.4 mm diameter, the gaps S and width W may be of the order of about 0.6 mm.

The electrodes 46.1, 46.2 and 46.3 of conductor 46 are electrically connected to a conductive ring 52 located on a radially recessed shoulder 54 of probe body 40 at its proximal end 56. The electrodes 48.1, 48.2 and 48.3 are electrically connected at the distal end 42 to a conductive lining 58 placed in a central through bore 59 of probe body 40. The lining 58 is in the form of a tube which extends from the proximal end 56 into lumen 34 of catheter 24 and has a central wash channel 57.

The fine electrodes have a gradually narrowing width at the distal end 42 to provide a generally consistent spacing between successively spaced electrodes while presenting a plurality of uniformly distributed opposite electrode pairs or poles around the longitudinal axis 50 for one or more bipolar contacts with tissue. With at least six electrode poles, hexapolar, spaced in fixed relationship around the distal end 42 and side of the peripheral surface 44 of probe body 40, at least bipolar and frequently higher polar tissue contact can be achieved substantially independent of the orientation of the probe body 40 relative to the tissue while achieving proper thermal heating of small tissue targets.

Electrical contact between electrodes 46.1, 46.2, 46.3 is made with conductor ring 52 as shown in FIG. 4 with respectively radial conductive segments 60.1, 60.2 and 60.3. Wire 30 is connected to ring 52 at a radial notch 62 in shoulder 54 where notch 62 is sized to receive conductor 64 of insulated wire 30. The notch 62 has a conductive coating 66 in electrical contact with ring 52 and soldered to conductor 64.

Electrical contact between electrodes 48.1, 48.2, 48.3 and wire 32 is made at the proximal end 56 where conductor 68 inside wire 32 is wrapped around and soldered to conductive tube 58. The connection of tube 58 to electrodes 48.1, 48.2 and 48.3 may be done with soldering.

In a current technique for the manufacture of the electrosurgical device 22 in accordance with the invention, the probe body 40 is formed of a machinable ceramic substrate such as sold under the tradename MACOR. The ceramic is cut into the desired shape, i.e. with semi-spherically shaped distal end 42, central bore 59, recessed shoulder 54 and notch 62. A conductive metallic compound is then painted, under a microscope, or by movement of the probe body relative to a thick film printing screen, on the cut ceramic substrate to form the conductor electrodes 46, 48 and ring 52.

The metallic compound preferably is formed of a material which upon the application of heat (firing) forms a strong fused bond with the ceramic substrate. Compounds for this purpose are well known in the semiconductor and electronic manufacture technology. The metallic compound is also preferably extended into the bore 59 followed by the insertion of tube 58 so that upon firing, an electrical connection is automatically made at the distal end between tube 58 and electrodes 48.1, 48.2 and 48.3. The thickness of conductor electrodes 46, 48 is quite thin, of the order of 0.025 mm (0.001").

With an electrosurgical device 22 in accordance with the invention, electrocoagulation can be obtained with various orientations of the probe body relative to the tissue and without requiring a rotation of the probe body. This is particularly advantageous when the device is used through an endoscope so that end-on, oblique or sidewise applications of the probe results in at least a bipolar contact.

With an electrosurgical device 22 in accordance with the invention, the electric field pattern around the probe body may be selected to provide homogeneous thermal heating close to the tissue surface contacted by the probe body. For example, in the above description of the electrosurgical device 22, the field lines 72 shown in FIG. 5 for a given field strength between adjacent conductor electrodes may be as generally illustrated in FIG. 5. The radial extent of the field lines 72 is a function of the size of the gap S between conductor electrodes. Thus, for some applications where a lesser radial field depth is desired to reduce the depth of coagulation, the gap between the fine electrodes may be reduced. In such case a larger number of electrodes can be employed resulting in a greater number of bipolar contacts. When a deeper tissue treatment is needed, the gas S between electrodes may be increased. The width of conductors and gap sizes may thus be selected, depending upon the particular physiological tissue being treated.

Some of the considerations in the selection of the width, W, to spacing, S, ratio relate to the heat distribution achieved in the tissue to be treated and the generation of tissue sticking problems. For example, a tissue sticking problem arises when a high concentration of heat causes too high a temperature in the tissue, generally greater than about 200° F., thus resulting in the adherence of tissue to metal parts of the probe body. If such condition occurs, the probe body requires frequent removal for cleaning and undesirably extends the duration of the treatment of the patient. When such excessive amount of heat is applied to stop a bleeding area, the resulting sticking of cauterized tissue also makes it difficult to disengage the probe body without removing the coagulated layer and thus restart bleeding.

Preferably, just enough electrical power, generally in the range from about 10 watts to about 25 watts for a 2.3 mm diameter probe, should be applied to dry the tissue area adjacent the probe to stop bleeding. The electrical power further should be applied in such manner that high voltage punch-through of cauterized dried tissue leading to sticking and/or unnecessary tissue wall damage is avoided. The electrical power normally is supplied in pulses having a duration of the order of one or several seconds.

Tissue sticking problems can be substantially avoided with an electrosurgical device in accordance with this invention since such structure enables the application of an adequate amount of electrical power at a relatively low voltage. The amount of power that can be applied is a function of the surface area of the probe conductors 46, 48 brought into contact with the tissue. When the surface area is relatively large, i.e. with an adequate conductor or electrode width, W, to spacing, S, ratio, there exists sufficient surface contact between an electrode and the tissue to supply electrical power at a relatively safe low voltage which is unlikely to force power through a dessicated layer causing deeper damage and risk of perforation.

Such safe low voltage is likely to be in the range of from about 30 to about 40 volts rms with a peak voltage generally less than about 60 volts. At higher altitudes where the tissue boiling point is lower, it is particularly desirable to keep the voltage low to avoid sticking problems.

The electrode tissue contact area tends to be a function of the ratio of the conductor width, W, to the spacing, S between conductors. At a low ratio, say less than about 1:3 or expressed in a fraction $\frac{1}{3}$, the minimum amount of power needed to stop bleeding requires a voltage more likely to be above the safe operating range. At such lower W:S ratio of about $\frac{1}{3}$ the probe 20 may provide the desired coagulating function; however, the impedance between the probe and tissue with such low ratio tends to be higher because the conductor surface in contact with tissue is less, thus requiring a higher voltage to transfer the desired amount of power into the tissue. This higher voltage tends to result in less uniform heating with hot spots that are likely to cause tissue sticking.

The W:S ratio, of the conductor width, W, to spacing, S, thus should be greater than about one-third ($\frac{1}{3}$) below which value less uniform heating with likelihood of sticking tends to occur. Preferably the W:S ratio is not less than about one-half ($\frac{1}{2}$). At W:S ratios of about 1:1 and 2:1 the probe tends to function adequately with good uniform heating. With a W:S ratio of 3:1, or expressed as 3, there is a tendency for less uniform heating but the presence of a relatively larger conductor surface area enables operation at a lower voltage which is safer from a standpoint of avoiding tissue sticking.

In FIG. 6 the electrodes are shown excited by a multiple phase RF source 76. Source 76 is a three phase source which is connected in a Y phase connection to electrodes 46.1, 46.2 and 46.3 with a return 78 connected to electrodes 48.1, 48.2 and 48.3. With the multiphase RF source 76, the voltage between electrodes such as 46.1 and 46.2 is larger than between electrodes 46.1 and 48.1, thus providing a stronger field for deeper coagulation. The connection of source 78 to probe body 40 involves four instead of two wires as in the embodiment of FIGS. 2–5.

In FIG. 7 an electrosurgical device 80 is shown using a similarly shaped probe body 40, but where electrodes are distributed in circumferential continuous bands 82.1 through 82.8. This arrangement is intended for tissue treatment of the inner wall of an anatomical tube. The electrodes 82.1 through 82.8 are oriented in planes which are transverse to the longitudinal axis 50.

Electrical connection between wires 30, 32 and electrodes 82 is made with a pair of electrical conductors 84, 86 located within bores drilled parallel to the longitudinal axis 50 of the device 80. A central bore 59 to contain a conductive liner-tube 58 is provided. Contact between conductors 84, 86 and the electrodes 82 is made through conductively lined or filled holes 88 located to intersect the desired electrode and conductor 84, 86 as illustrated in FIG. 7.

The conductor 84 is similarly connected to ring electrode 52 to which wire 30 is soldered. Conductor 86 is connected to the conductive tubing 58 together with the conductor of wire 32. Manufacture of the electrosurgical device 80 may be done similarly as suggested for the device shown in FIG. 2.

Having thus described an electrosurgical device in accordance with the invention, its advantages can be appreciated. The central wash channel through tube 58 is particularly useful in clearing the tissue area precisely ahead of the electrosurgical device. The channel or tube is, therefore, made sufficiently wide to accomodate the desired flow of liquid or gas. The fluid may be passed as illustrated through lumen 34 of catheter 24 in between the wires 30, 32 or, if space permits, a separate conduit can be used which fits inside lumen 34 and fits over the proximal end of tube 58. The conductive lining 58 for bore 59 in the probe body 40 may in some applications be dispensed with. In such case electrical contact with electrodes 48.1, 48.2 and 48.3 can be provided from a split conductor ring 52 to which wires 30, 32 are then connected.

With the geometrical arrangement and distribution of fine electrodes on an electrosurgical device as shown in FIGS. 2–5, the advantages of bipolar tissue treatment are obtained and, in particular, an ability to randomly approach a tissue target area either side-wise, head-on or obliquely, without a loss of an ability to treat the target area. The incorporation of a central wash channel further enhances the utility of the electrosurgical device.

Variations from the described embodiments may be made by one skilled in the art without departing from the scope of the invention.

What is claimed is:

1. An electrosurgical device for use in the treatment of tissue comprising:

a multipolar probe body sized to enable passage of the probe body through an endoscope channel, said probe body having a peripheral surface and a longitudinal axis extending from a proximal to a distal end of the probe body;

at least one electrically isolated conductor pair mounted on the probe body including means for connecting the conductor pair to a source of electrical energy, each conductor comprising at least two electrodes with each electrode of one conductor being separated from and being interposed with another electrode of the other conductor with a spacing therebetween, said different electrodes being further so distributed and respectively so sized in width and length so as to extend in spaced apart relationship over the distal end and over the peripheral surface side which is located radially from said longitudinal axis, the ratio of the width of electrodes to the spacing between the different electrodes being so selected as to enable effective bipolar treatment of tissue with effectively omnidirectional probe body orientations relative to the tissue to be treated when the probe body is used.

2. The electrosurgical device as claimed in claim 1 wherein said ratio of the width of the electrodes to said spacing is selected to be at least greater than about one-third.

3. The electrosurgical device as claimed in claim 2 wherein said ratio lies in a range extending from about one half to about three.

4. The electrosurgical device as claimed in claim 1 wherein said ratio of the electrode width to said spacing is at least about unity.

5. The electrosurgical device as set forth in claim 1 wherein the conductors on the probe body are each branched into at least three electrodes extending over the distal end and side of the peripheral surface.

6. The electrosurgical device as claimed in claim 5 wherein each conductor is formed of at least three electrodes which are aligned parallel to the longitudinal axis along the peripheral side of the probe body.

7. The electrosurgical device as claimed in claim 6 wherein said probe body is smoothly curved at the distal end, said electrodes extending onto said distal end of the probe body to provide multiple bipolar contacts around the longitudinal axis of the probe body at said distal end.

8. The electrosurgical device as claimed in claim 1 wherein said probe body is formed of a rigid insulative material with a fluid channel extending through the rigid insulative material from a proximal to a distal end thereof, said fluid channel being sized to pass fluid to clear the tissue area to be treated.

9. The electrosurgical device as claimed in claim 6 wherein said fluid channel is provided with a conductive lining which is electrically connected to one of said electrically isolated conductors.

10. The electrosurgical device as claimed in claim 9 wherein said probe body has a generally blunt shaped distal end with a generally central opening therein corresponding to a distal end of said electrically conductive fluid channel, and wherein the conductor connected to the conductive lining includes a plurality of electrodes which extend over said shaped distal end of the probe body to connect to said conductive lining at the distal end, and wherein the other conductor includes a plurality of electrodes which extend over the distal end and terminate in spaced relationship from the electrodes connected to the conductive lining to form multipolar contact capability at the distal end of the probe body.

11. The electrosurgical device as claimed in claim 10 wherein electrodes are distributed at about equiangular spacing of the order of about 60° about the longitudinal axis.

12. An electrosurgical device in accordance with claim 1, 2, 3, 4, 5, 8, 9, 10 or 11 wherein said conductors are thin metallized strips fused to the peripheral surface of the probe body to maintain a generally smooth external probe body surface.

13. The electrosurgical device as claimed in claim 10 wherein the probe body is further provided with a radially recessed annular shoulder at the proximal end and a ring electrode placed around the recessed shoulder and electrically connected to electrode of one of said conductors on the probe body.

14. The electrosurgical device as set forth in claim 13 wherein the recessed shoulder further is provided with a radially recessed notch sized to receive a wire connection.

15. The electrosurgical device as claimed in claim 1, 2, 3, 4, 5, 8, 9, 10 or 11 wherein said conductors are each formed of generally like sized and uniformly distributed fine strip electrodes fused to the outer peripheral surface of the probe body.

16. The electrosurgical device as claimed in claim 15 wherein said conductors each include at least three electrically connected longitudinal electrodes disposed generally parallel to the longitudinal axis on said peripheral surface of the probe body, with electrodes which are connected to different conductors being respectively successively circumferentially spaced from each other to provide said at least bipolar tissue contact capability around the periphery of the probe body.

17. The electrosurgical device as claimed in claim 1, 2, 3, 4, 8, 9, 10 or 11 wherein each conductor is formed with circular bands located on the peripheral surface and extending around the longitudinal axis.

18. An electrosurgical device for use in the treatment of tissue comprising:

an insulative probe body having a peripheral surface and a longitudinal axis extending from a proximal to a distal end of the probe body, said probe body being sized to pass through the channel of an endoscope;

electrically isolated conductors mounted on the probe body including means to connect the conductors to a source of electrical energy, said conductors being each formed with a plurality of fine strip shaped electrodes fused to the peripheral probe body surface, with electrodes of different conductors being respectively interposed with each other in fixed relationship on the peripheral surface of the probe body, said electrodes of different conductors being further respectively so sized and distributed so as to extend in spaced apart pairs over the distal end and over the radial side of said peripheral surface generally parallel with the longitudinal axis, with at least three of said electrode pairs being arranged on the probe body to enable at least bipolar treatment of tissue with effectively omnidirectional orientations of the probe body relative to the tissue to be treated when the probe body is used, the probe body being provided with a hollow conductive material located inside the probe body and extending from a proximal location of the probe body to its distal end, said conductive material being electrically connected at said distal end to the electrodes forming one of said conductors;

said hollow conductive material forming a fluid channel extending through the probe body from a proximal to a distal end thereof to pass fluid to clear tissue area to be treated, and wherein said electrodes forming the other of said conductors extend over the distal end of the probe body and terminiate in spaced relationship from the distal end of the conductive material to form a plurality of bipolar electrode pairs over the probe body distal end.

19. The electrosurgical device as claimed in claim 18 wherein said conductive material is in the form of a hollow conductive tube.

20. An electrosurgical device for use in the treatment of tissue comprising:

a multipolar probe body sized to enable passage of the probe body through an endoscope channel, said probe body having a peripheral surface and a longitudinal axis extending from a proximal to a distal end of the probe body;

electrically isolated conductor pairs mounted on the probe body including means for connecting the conductors to a source of electrical energy, with one conductor being interposed with another conductor with a spacing therebetween, said different conductors being further so distributed and respectively so sized in width and length so as to extend in spaced apart relationship over the distal end and over the peripheral surface side which is located radially from said longitudinal axis, the ratio of the width of conductors to the spacing between the different conductors being so selected as to enable effective bipolar treatment of tissue with effectively omnidirectional probe body orientations relative to the tissue to be treated when the probe body is used.

21. A method of bipolar electrosurgical coagulation of a bleeding tissue site with the use of high frequency electrical power comprising the step of:

applying from a distal end of a channel of an endoscope the electrical power to the bleeding site through at least a pair of spaced apart conductors having respective surface areas thereof in contact with the site to cause a coagulation of the bleeding tissue site, each conductor having at least two electrodes, the magnitude of said surface areas of the conductors and the spacing between the conductors being so selected as to obtain a generally uniform electrical heating of the bleeding site and a coagulation thereof without sticking of the conductors to the coagulated bleeding site, the ratio of the width of conductors to the spacing between the different conductors being so selected as to enable effective bipolar treatment of tissue with effectively omnidirectional orientations of the body upon which the conductors are on relative to the tissue to be treated.

22. The method as claimed in claim 21 wherein said electrical power applying step further includes the application of said electrical power to the bleeding site through spaced apart conductors which are so sized and located that the ratio of the width of the conductors to the spacing between them is sufficient to obtain said uniform heating and said coagulation without sticking.

23. The method as claimed in claim 22 wherein said electrical power applying step further includes the application of electrical power through conductors whose width and spacing is selected so that the ratio of said width to said spacing is greater than about one-third.

24. The method as claimed in claim 23 wherein the application of electrical power through conductors whose width and spacing is selected so that the ratio of said width to said spacing lies between about one-half to about three.

25. The method as claimed in claim 24 and further including the step of:

supplying said electrical power about a surface area in a generally uniformly distributed manner so as to provide a generally omnidirectionally available source of electrical coagulating power from the distal end of the endoscope.

* * * * *